United States Patent
Minium

(10) Patent No.: US 7,845,941 B2
(45) Date of Patent: *Dec. 7, 2010

(54) ORTHODONTIC INSTRUMENT FOR USE WITH ADJUSTABLE ORTHODONTIC APPARATUS

(76) Inventor: Mark Minium, 1141 Dry Powder Cir., Mechanicsburg, PA (US) 17050

(*) Notice: Subject to any disclaimer, the term of this patent is extended or adjusted under 35 U.S.C. 154(b) by 0 days.

This patent is subject to a terminal disclaimer.

(21) Appl. No.: 12/241,548

(22) Filed: Sep. 30, 2008

(65) Prior Publication Data

US 2009/0117512 A1 May 7, 2009

Related U.S. Application Data

(63) Continuation-in-part of application No. 12/203,479, filed on Sep. 3, 2008, which is a continuation-in-part of application No. 12/072,062, filed on Feb. 25, 2008, which is a continuation-in-part of application No. 11/982,199, filed on Nov. 2, 2007, now Pat. No. 7,731,496, application No. 12/241,548, filed on Sep. 30, 2008, which is a continuation-in-part of application No. 12/214,218, filed on Jun. 18, 2008, now Pat. No. 7,740,475, and a continuation of application No. 12/072,062, which is a continuation-in-part of application No. 11/982,199, application No. 12/241,548, which is a continuation-in-part of application No. 11/982,199.

(51) Int. Cl.
A61C 7/04 (2006.01)
A61C 7/12 (2006.01)

(52) U.S. Cl. .............................. 433/16; 433/4

(58) Field of Classification Search .................. 433/3, 433/4, 153, 156, 157, 159, 8–16; 606/99, 606/103, 104, 157, 158, 205, 206, 208, 210, 606/211; 600/141, 201; 294/99.2; 81/300, 81/302, 415; D24/133, 143, 147; D8/52, D8/54
See application file for complete search history.

(56) References Cited

U.S. PATENT DOCUMENTS

| 1,874,257 | A | * | 8/1932 | Doptis ............... 29/213.1 |
| 1,974,106 | A | | 9/1934 | Gardella |
| 2,334,252 | A | * | 11/1943 | MacGregor ........... 294/99.2 |
| 2,379,011 | A | | 6/1945 | Laskin |
| 2,595,683 | A | | 5/1952 | Monte |
| 2,634,728 | A | | 4/1953 | Dale |
| 3,203,098 | A | | 8/1965 | Petraitis |
| 3,218,712 | A | | 11/1965 | Wallshein |
| 3,291,476 | A | | 12/1966 | Calkin |
| 3,421,221 | A | | 1/1969 | Silverman et al. |
| 3,423,833 | A | | 1/1969 | Pearlman |
| 3,461,559 | A | | 8/1969 | Silverman et al. |
| 3,464,113 | A | | 9/1969 | Silverman et al. |
| 3,721,005 | A | | 3/1973 | Cohen |
| 3,871,098 | A | | 3/1975 | Dean |
| 3,946,488 | A | | 3/1976 | Miller et al. |
| 4,001,940 | A | | 1/1977 | Cusato |

(Continued)

*Primary Examiner*—Cris L Rodriguez
*Assistant Examiner*—Michael R Ballinger

(57) ABSTRACT

An instrument is provided, having a handle and at least one working end. In a first embodiment, the working end has a first leg and a second leg, the second leg for disengaging a spring clip. In a second embodiment, the working end has a first leg and a second leg for grasping a connector plate of an orthodontic bracket, and a depth limiter attached to the first leg for preventing inadvertent grasping of an orthodontic bracket base plate.

21 Claims, 18 Drawing Sheets

U.S. PATENT DOCUMENTS

| | | | |
|---|---|---|---|
| 4,009,899 A * | 3/1977 | Johnson | 294/33 |
| 4,035,919 A | 7/1977 | Cusato | |
| 4,139,945 A | 2/1979 | DiGiulio | |
| 4,161,066 A | 7/1979 | Morrow et al. | |
| 4,243,387 A | 1/1981 | Prins | |
| 4,353,692 A | 10/1982 | Karrakussoglu | |
| 4,487,580 A | 12/1984 | Ridgeway | |
| 4,487,581 A | 12/1984 | Adler | |
| 4,597,739 A | 7/1986 | Rosenberg | |
| 4,676,746 A * | 6/1987 | Klapper | 433/16 |
| 4,786,252 A | 11/1988 | Fujita | |
| 4,867,678 A | 9/1989 | Parker | |
| 4,917,602 A | 4/1990 | Broussard | |
| 5,039,302 A * | 8/1991 | Keys | 433/3 |
| 5,094,614 A | 3/1992 | Wildman | |
| 5,520,704 A | 5/1996 | Castro et al. | |
| 5,711,666 A | 1/1998 | Hanson | |
| 5,868,787 A | 2/1999 | Kim | |
| 5,906,486 A | 5/1999 | Hanson | |
| 5,954,502 A | 9/1999 | Tuenge et al. | |
| 6,190,166 B1 | 2/2001 | Sasakura | |
| 6,248,123 B1 * | 6/2001 | McDonald | 606/210 |
| D456,076 S * | 4/2002 | Tyler | D24/143 |
| 6,447,291 B2 | 9/2002 | Kim | |
| 6,733,286 B2 | 5/2004 | Abels et al. | |
| 6,786,719 B2 | 9/2004 | McGann | |
| 7,104,791 B2 | 9/2006 | Hanson | |
| 7,267,545 B2 | 9/2007 | Oda | |
| 2002/0006595 A1 * | 1/2002 | Voudouris | 433/4 |
| 2004/0072117 A1 | 4/2004 | Farzin-Nia et al. | |
| 2005/0125029 A1 * | 6/2005 | Bernard et al. | 606/205 |
| 2006/0008761 A1 | 1/2006 | Allred | |
| 2006/0154196 A1 | 7/2006 | Oda | |
| 2006/0263737 A1 | 11/2006 | Oda | |
| 2007/0092849 A1 * | 4/2007 | Cosse | 433/8 |
| 2007/0224569 A1 | 9/2007 | Oda | |

* cited by examiner

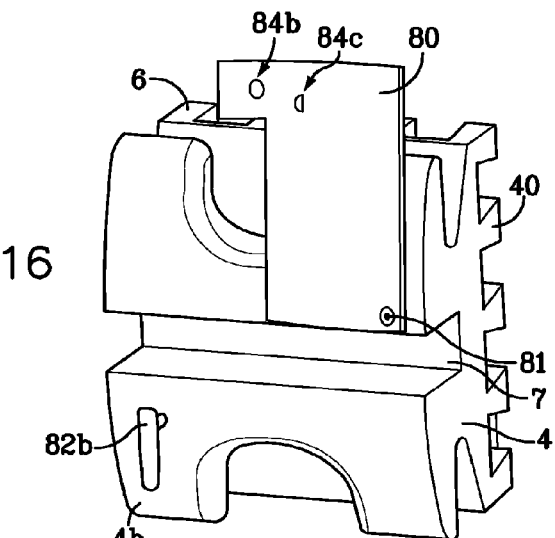
FIG. 16
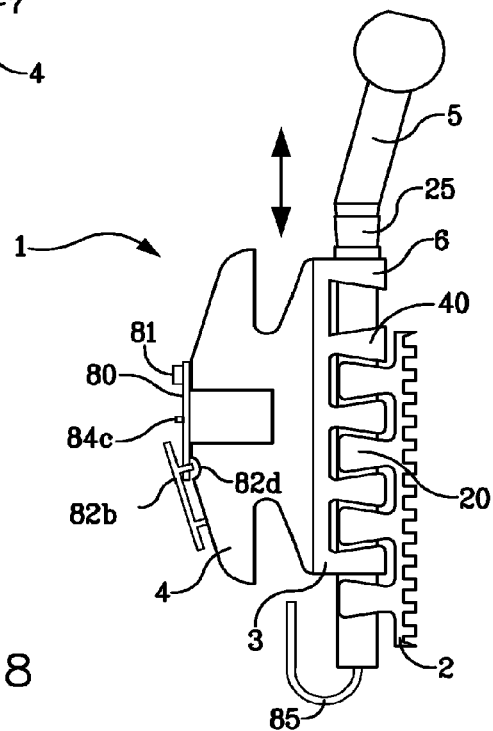
FIG. 17
FIG. 18

US 7,845,941 B2

ORTHODONTIC INSTRUMENT FOR USE WITH ADJUSTABLE ORTHODONTIC APPARATUS

CROSS REFERENCE TO RELATED APPLICATIONS

This application is a continuation-in-part of U.S. application Ser. No. 12/203,479, entitled "Orthodontic Apparatus With Self-Ligating Bracket and Locking Device", filed on Sep. 3, 2008, which is a continuation-in-part of U.S. application Ser. No. 12/072,062, entitled "Orthodontic Apparatus With Self-Ligating Bracket", filed on Feb. 25, 2008, which is a continuation-in-part of U.S. application Ser. No. 11/982,199 entitled "Adjustable Orthodontic Apparatus", filed on Nov. 2, 2007; and a continuation-in-part of U.S. application Ser. No. 12/214,218, entitled "Orthodontic Apparatus With Adjustable Base Plate And Connecting Plate", filed on Jun. 18, 2008, which is a continuation-in-part of U.S. application Ser. No. 11/982,199 entitled "Adjustable Orthodontic Apparatus", filed on Nov. 2, 2007 and a continuation of U.S. application Ser. No. 12/072,062, entitled "Orthodontic Apparatus With Self-Ligating Bracket", filed on Feb. 25, 2008; and a continuation-in-part of U.S. application Ser. No. 11/982,199 entitled "Adjustable Orthodontic Apparatus", filed on Nov. 2, 2007; all incorporated by reference herein.

FIELD OF THE INVENTION

This invention relates to an orthodontic treatment apparatus and in particular, to an orthodontic instrument for use with adjustable orthodontic apparatus.

BACKGROUND OF THE INVENTION

The science of orthodontics has been advancing at a rapid pace. Stainless steel wires traditionally used to apply orthodontic forces to teeth have in large part been replaced by high-tech alloy wires. These more flexible "memory" archwires employ the use of titanium, niobium, copper and other more efficient materials. Heat activated, these wires allow for lower, longer acting forces with more allowable deflection of the wire to engage brackets adhered to malpositioned teeth. Once engaged, the archwires are maintained within the brackets using steel ligatures, elastomeric ties, and most recently, self-ligating brackets of various designs.

Bracket placement has always been important in orthodontic therapy; the introduction of the self-ligating bracket has increased its importance. Because bracket position directly effects the force application of the archwire on, and ultimately the final position of, the tooth, proper bracket placement during treatment is critical. To aid in the positioning of the bracket at a tooth location which will bring the teeth to a desired physiologic final dental arch form, positioning instruments have been developed, indirect bonding has been used, and most recently, computer aided indirect bonding has been introduced.

Even using the newest and most advanced types of orthodontic brackets, a treatment visit is still required at about 6 months after the initial application of the brackets in order to refine bracket position to better achieve desired physiologic parallel root form. Using radiographic images for root repositioning guidance, this treatment visit is scheduled for all patients and often needs to be to be repeated during the treatment course, resulting in multiple time consuming bracket repositioning visits.

Sliding, reduced friction mechanics, the basis of modern orthodontic therapy, relies on using high-tech memory wires without bends. Because the metallurgic properties of modern high tech wires do not permit bending of these wires to compensate for less than ideal bracket placement, final tooth position is dependent upon ideal bracket placement. Therefore, during the course of treatment, additional time consuming bracket repositioning visits must be scheduled for those teeth that could not accommodate initial ideal bracket placement, further adding both time and expense to orthodontic treatment.

Bracket holders typically used in orthodontics are the self closing type which allow the operator to grip the bracket by the wings exposing the back mesh pad for application of the bonding material. Using the bracket holder, the bracket is positioned by the clinician onto the outer surface of the tooth. Typically, the bracket holder grips and holds a bracket while in its neutral, or resting state. After proper positioning of the bracket, the bracket holder is disengaged from the bracket by squeezing the bracket holder handle.

The adjustable orthodontic apparatus described in detail below presents new challenges for bracket holders. For example, the bracket holder must easily engage a connector portion of the adjustable bracket, yet not engage the base portion, thereby permitting easy repositioning of the connector portion in relation to the base portion.

Accordingly, there is still a continuing need for improved orthodontic instrument designs. The present invention fulfills this need and further provides related advantages.

BRIEF SUMMARY OF THE INVENTION

In a first embodiment, to overcome these bracket repositioning problems, the present invention provides for an orthodontic bracket holder which comprises a handle, a working end comprising opposing beaks, and a depth limiter attached to one beak and slidably received by the other beak.

In another embodiment, the present invention relates to an orthodontic instrument for disengaging a self ligating bracket locking member comprising a handle and a working end comprising two legs, the first leg for engaging a first bracket portion, the second leg to disengage the locking member.

One advantage of the present invention is the ability to easily and rapidly engage a bracket connector plate while not engaging a bracket base plate.

Other features and advantages of the present invention will be apparent from the following more detailed description of the preferred embodiments, taken in conjunction with the accompanying drawings which illustrate, by way of example, the principles of the invention.

BRIEF DESCRIPTION OF THE DRAWINGS

The accompanying drawings are included to provide a further understanding of the present invention. These drawings are incorporated in and constitute a part of this specification, illustrate one or more embodiments of the present invention, and together with the description, serve to explain the principles of the present invention.

FIG. 16 is a front perspective view of the self ligating bracket and locking pin in an open position;

FIG. 17 is a front perspective view of the self ligating bracket and locking pin in a closed position;

FIG. 18 is a side view of self ligating bracket with locking system; and

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessary to scale, and some features may be exaggerated to show details of particular components. Therefore, specific structural and functional details disclosed herein are not to be interpreted as limiting, but merely as a basis for the claims and as a representative basis for teaching one skilled in the art to variously employ the present invention.

For purposes of this invention, a bracket is defined as any device which is fixed to the surface of a tooth and designed for attachment of archwires or auxiliaries such as for example, springs or elastics; used to transmit forces from these archwires and/or auxiliaries to the tooth and its supporting structures.

In most cases, tooth moving forces are stored in the archwire and/or auxiliaries and delivered through a bracket to the tooth and supporting structures by deflection of the archwire or auxiliary from a passive to an active state.

Traditionally, a bracket comprises a base; one or more archwire slots designed for receiving an archwire; and occlusal and gingival flanges or wings designed to receive elastic or metal ligatures used to maintain the archwire within the slot. The bracket is affixed to a tooth by direct bonding through the use of a mesh pad incorporated into the back of the bracket or the bracket is welded or brazed to a band which is cemented around the tooth. Newer, self ligating bracket designs incorporate, for example, a sliding door that closes over the slot, thereby holding the wire in place and obviating the need for separate ligatures.

Figure 1:
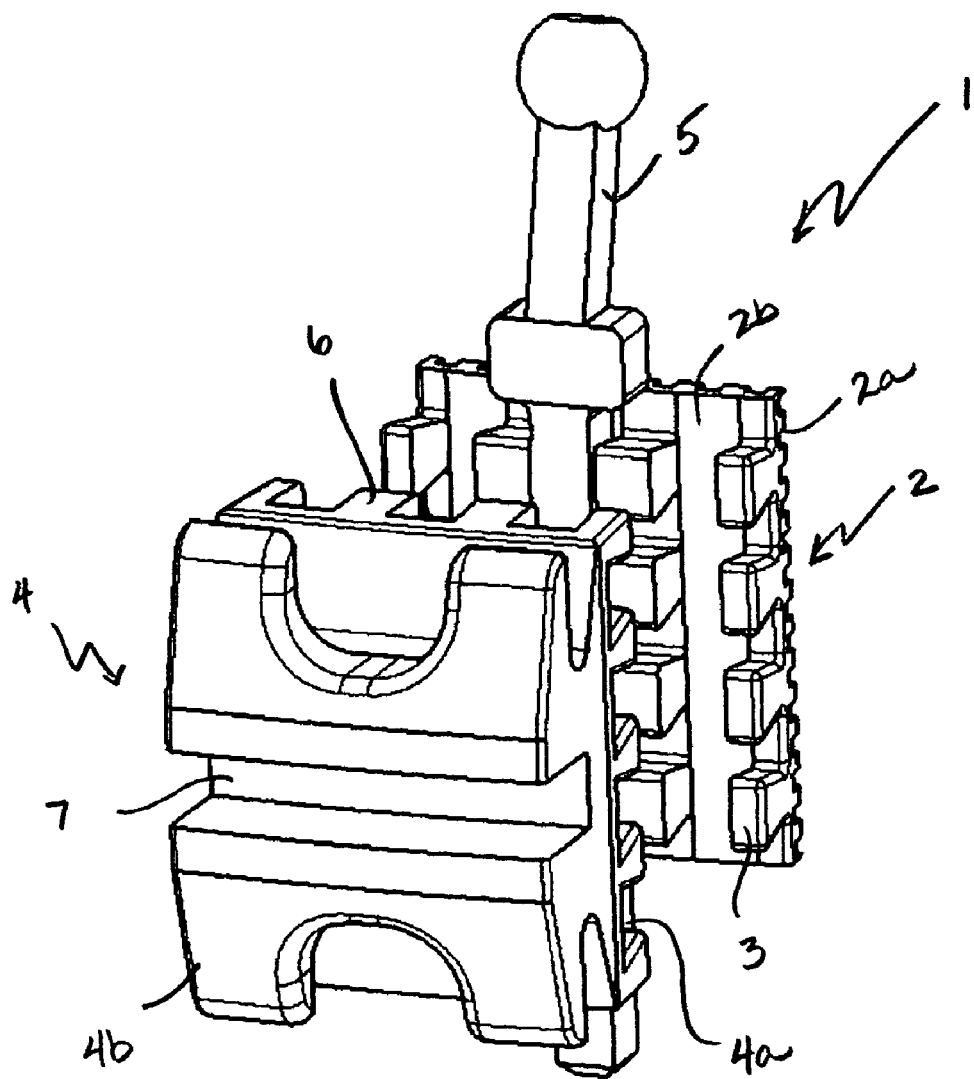
FIG. 1 is an exploded view of one of the embodiments of the present invention.
Figure 2:
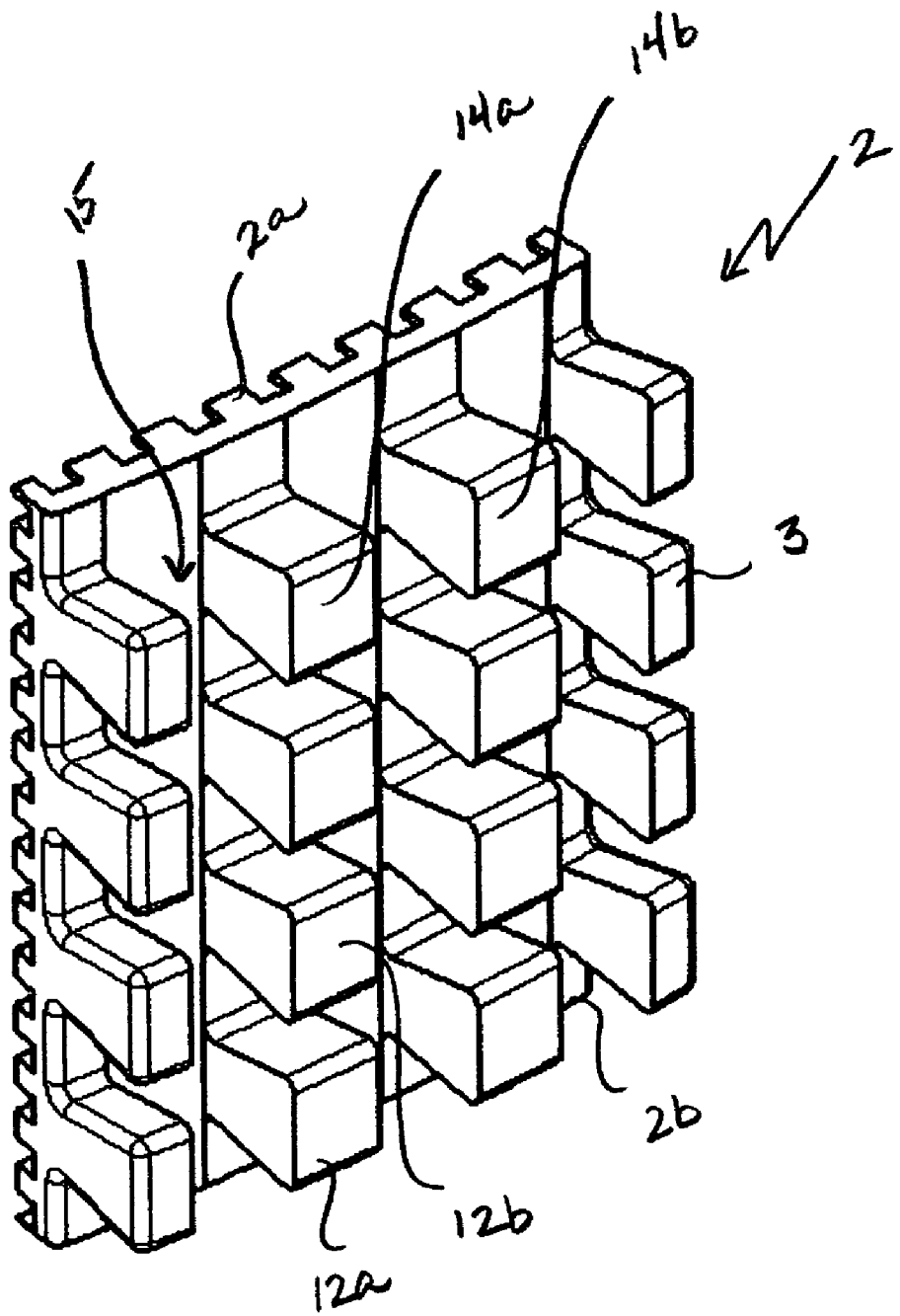
FIG. 2 is a front perspective view of one of the embodiments of the base plate of the present invention.
Figure 3:
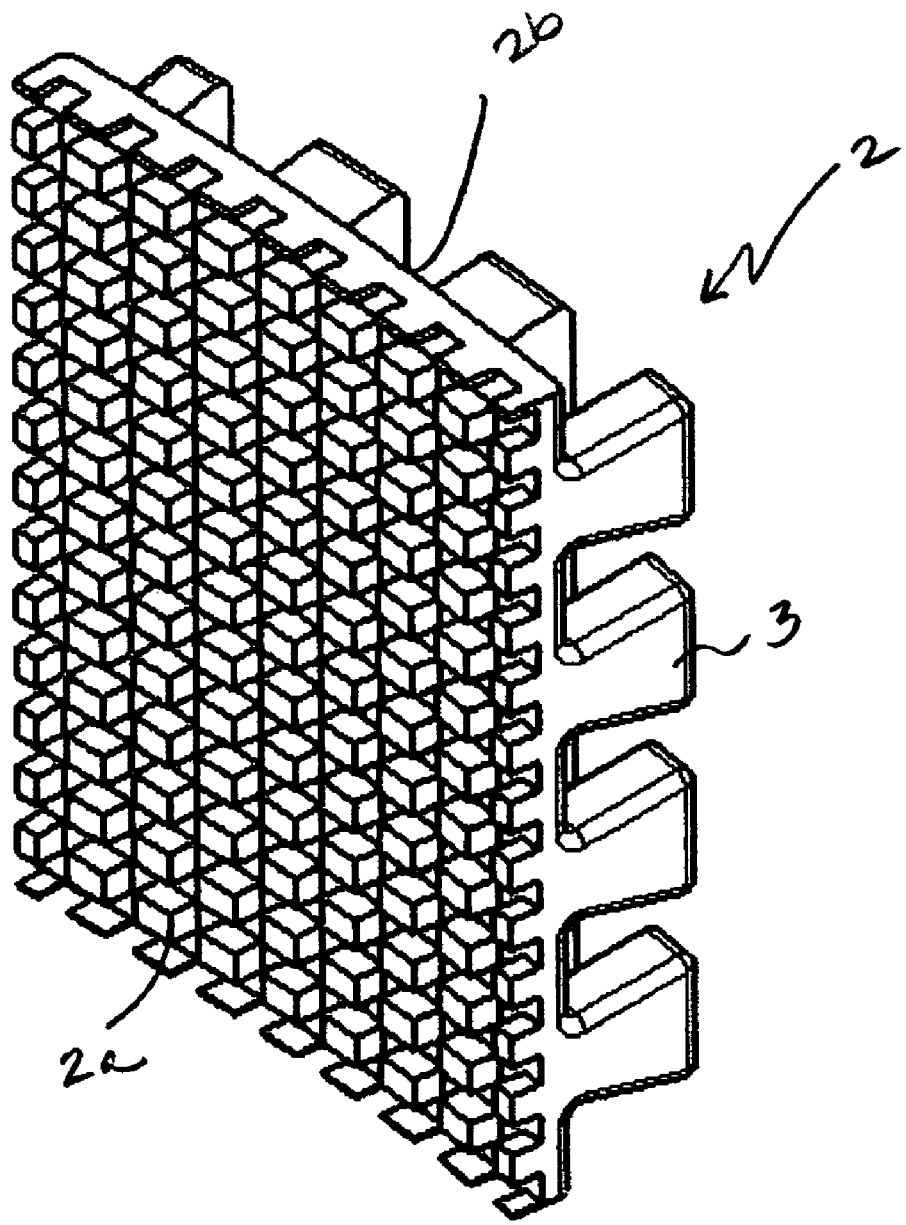
FIG. 3 is a back perspective view of the base plate in FIG. 2.
Figure 4:
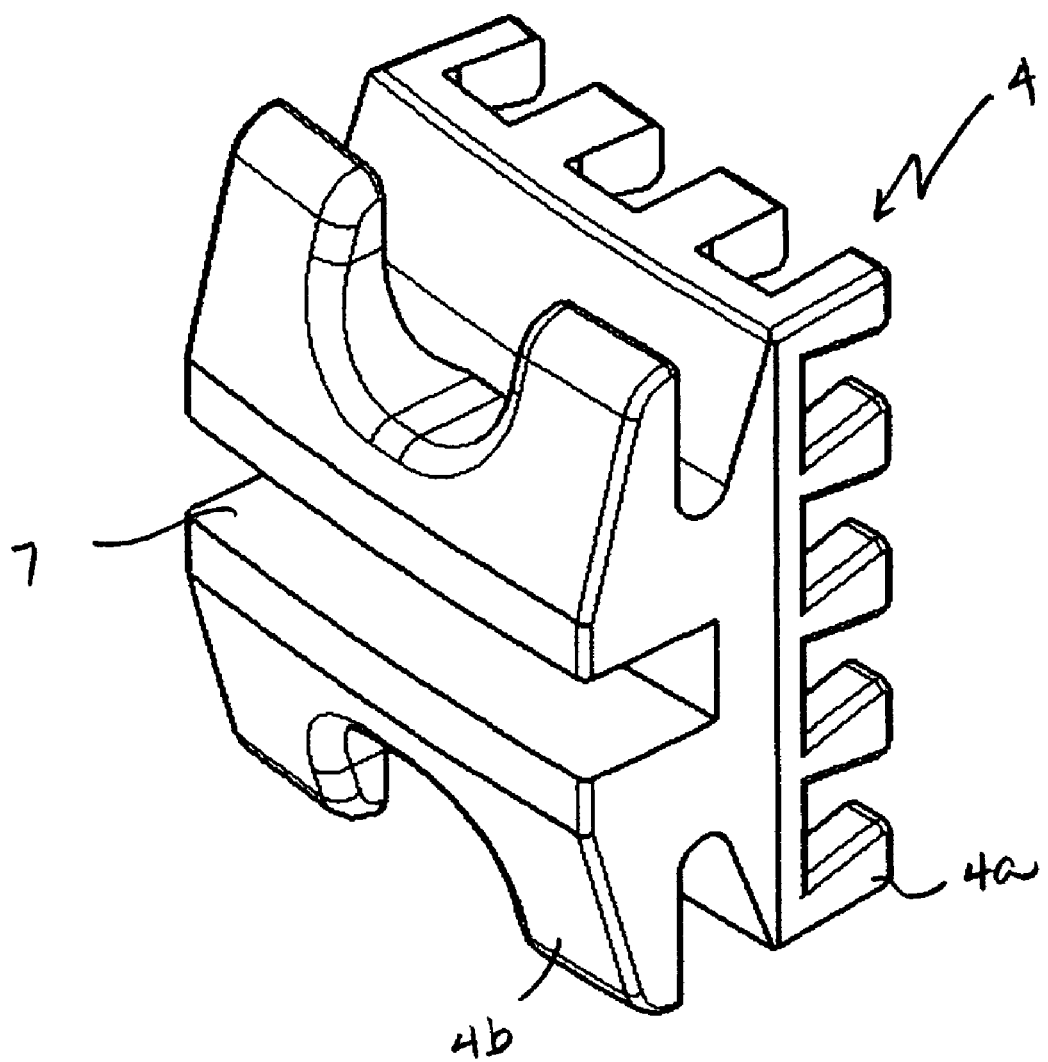
FIG. 4 is a frontal perspective view of one of the embodiments of the connecting plate of the present invention.
Figure 5:
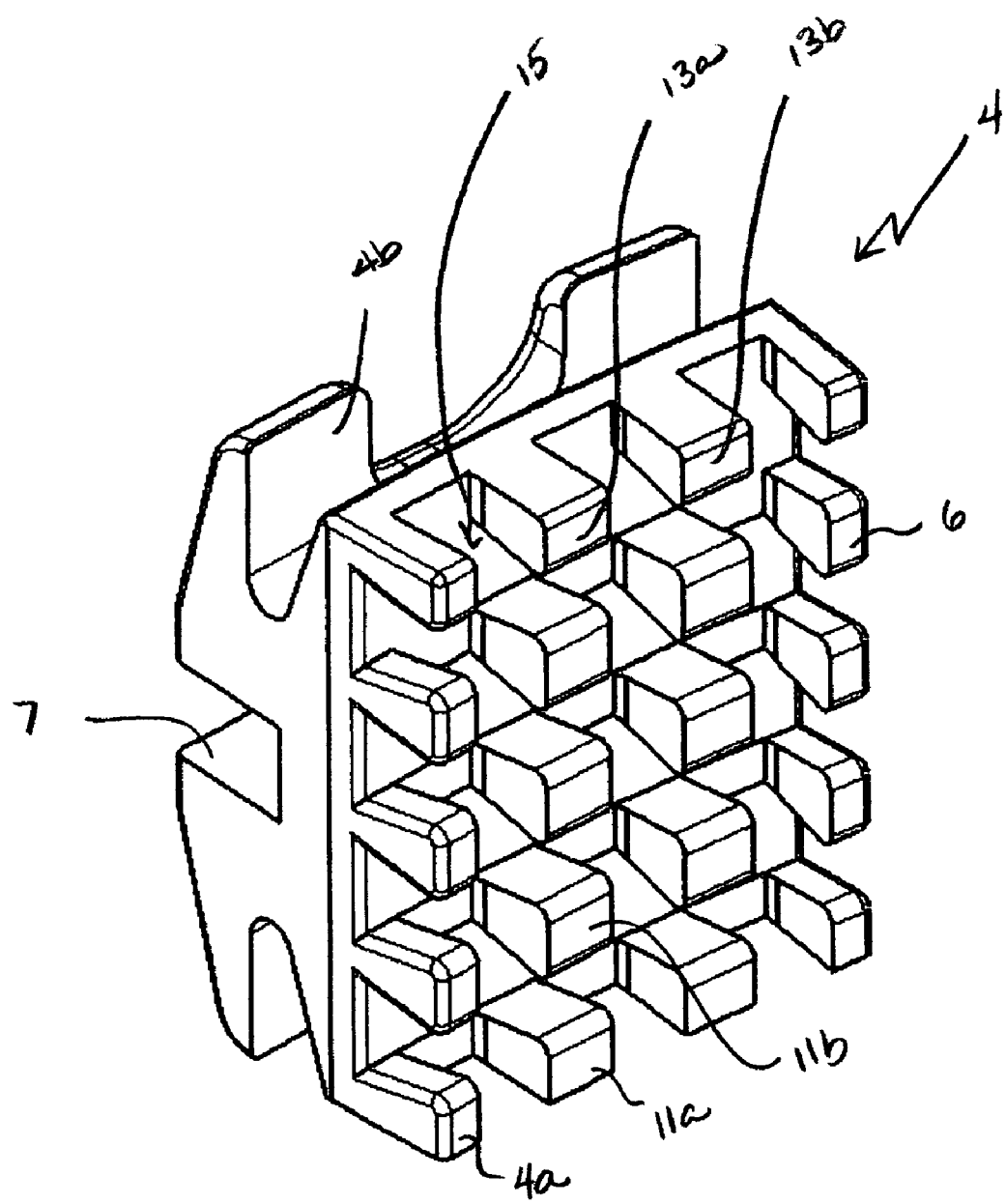
FIG. 5 is a back perspective view of the connecting plate in FIG. 4.

Turning now to the figures, FIG. 1 illustrates one of the embodiments of the present invention. More specifically, an adjustable orthodontic apparatus 1 is provided. The apparatus 1 comprises a base plate 2 comprising opposing sides, 2a and 2b respectively, a first side 2a being a tooth engaging side and a second side 2b comprises a first device 3 for engaging and adjusting the vertical and horizontal position of a connecting plate 4. The connecting plate 4 has opposing sides, 4a and 4b respectively, a first side 4a comprises a second device 6 for engaging the second side 2b of the base plate 2 and allowing for the vertical and horizontal movement of the connecting plate 4 as it relates to the base plate 2. The apparatus 1 further comprises a securing device 5 for locking the connecting plate 3 to a desired position onto the base plate 2.

The securing device 5 for locking the base plate 2 to the connecting plate 3 comprises, for example, a pin. The second side 4b of the connecting plate 4 comprises an orthodontic device 7. The orthodontic device 7 may be, for example, an archwire receiving bracket or an archwire receiving eyelet.

FIGS. 2-5 relate to the front and back views of the base plate 2 and connecting plate 4 of the present invention. The first device 3 of the second side 2b of the base plate 2 comprises at least two vertically positioned protrusions, 12a and 12b respectively, and at least two horizontally positioned protrusions, 14a and 14b respectively, and the second device 6 of the first side 4a of the connecting plate 4 comprises at least two vertically positioned protrusions, 11a and 11b respectively, and at least two horizontally positioned protrusions, 13a and 13b respectively.

There are a plurality of spaces in between each of the protrusions, 11a, 11b, 12a, 12b, 13a, 13b, 14a and 14b respectively, in the second side 2b of the base plate 2 and the first side 4a of the connecting plate 4. The plurality of spaces provides for channels 15 for protrusions, 11a, 11b, 12a, 12b, 13a, 13b, 14a and 14b respectively, to move during adjustment of the connecting plate 4 relative to the base plate 2 (described in greater detail below) and the securing device 5 is situated within the channel 15 when the connecting plate 4 is locked onto the base plate 2.

Figure 6:
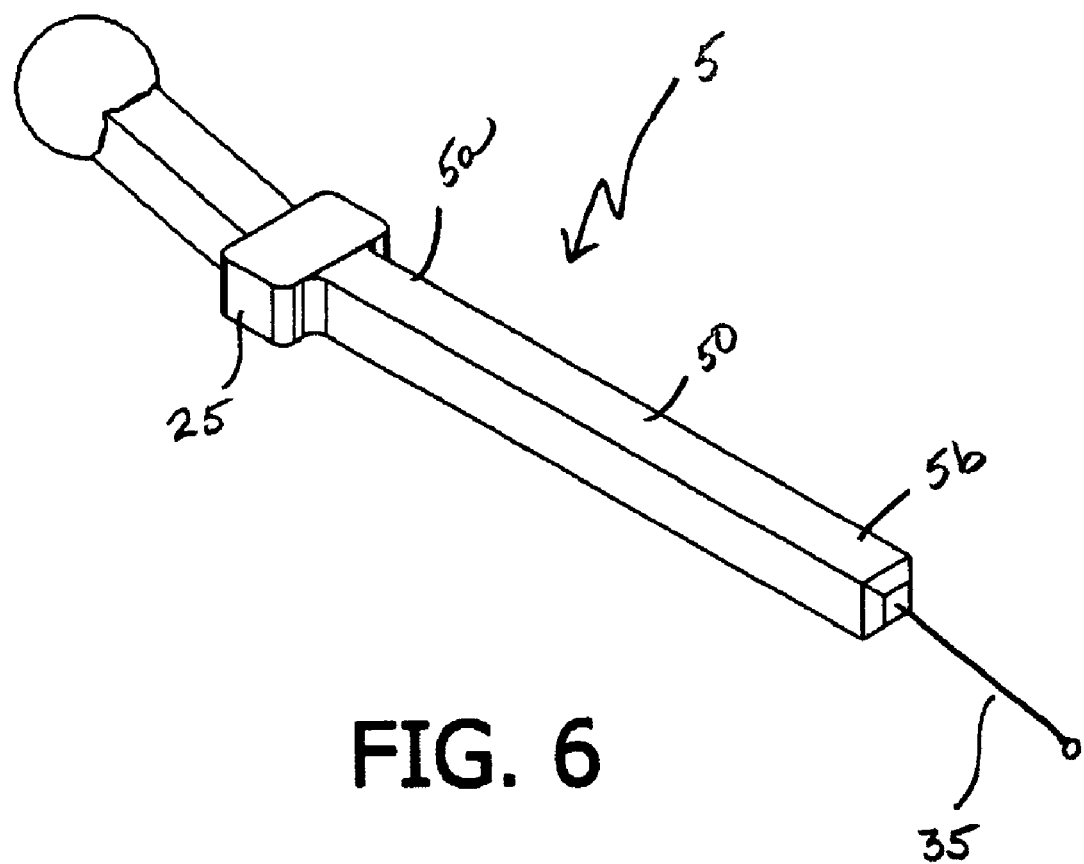
FIG. 6 is a perspective view of the securing device of the present invention.

FIG. 6 illustrates the securing device 5 which comprises an elongated shaft 50 designed to fit within the channels between the protrusions and also has opposing ends, 5a and 5b respectively. One side 5a has extended stop portion 25 and the opposing side 5b has a bendable portion 35 designed to lock the position of the connecting plate to the base plate. In another embodiment, side 5a is slightly bent at an angle.

Figure 7:
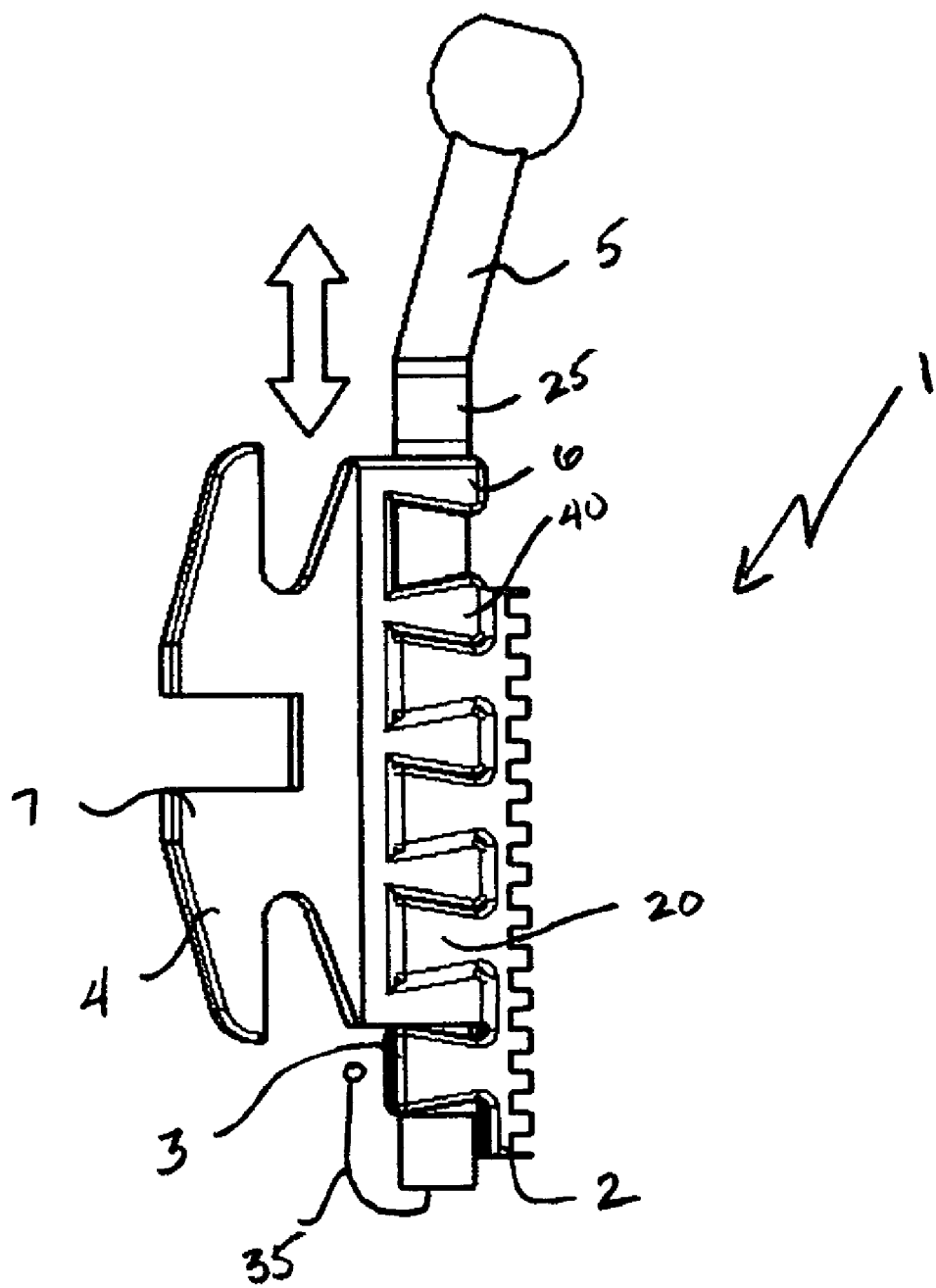
FIG. 7 is a side perspective view of the interaction of the connecting plate and the base plate of the present invention.
Figure 8:
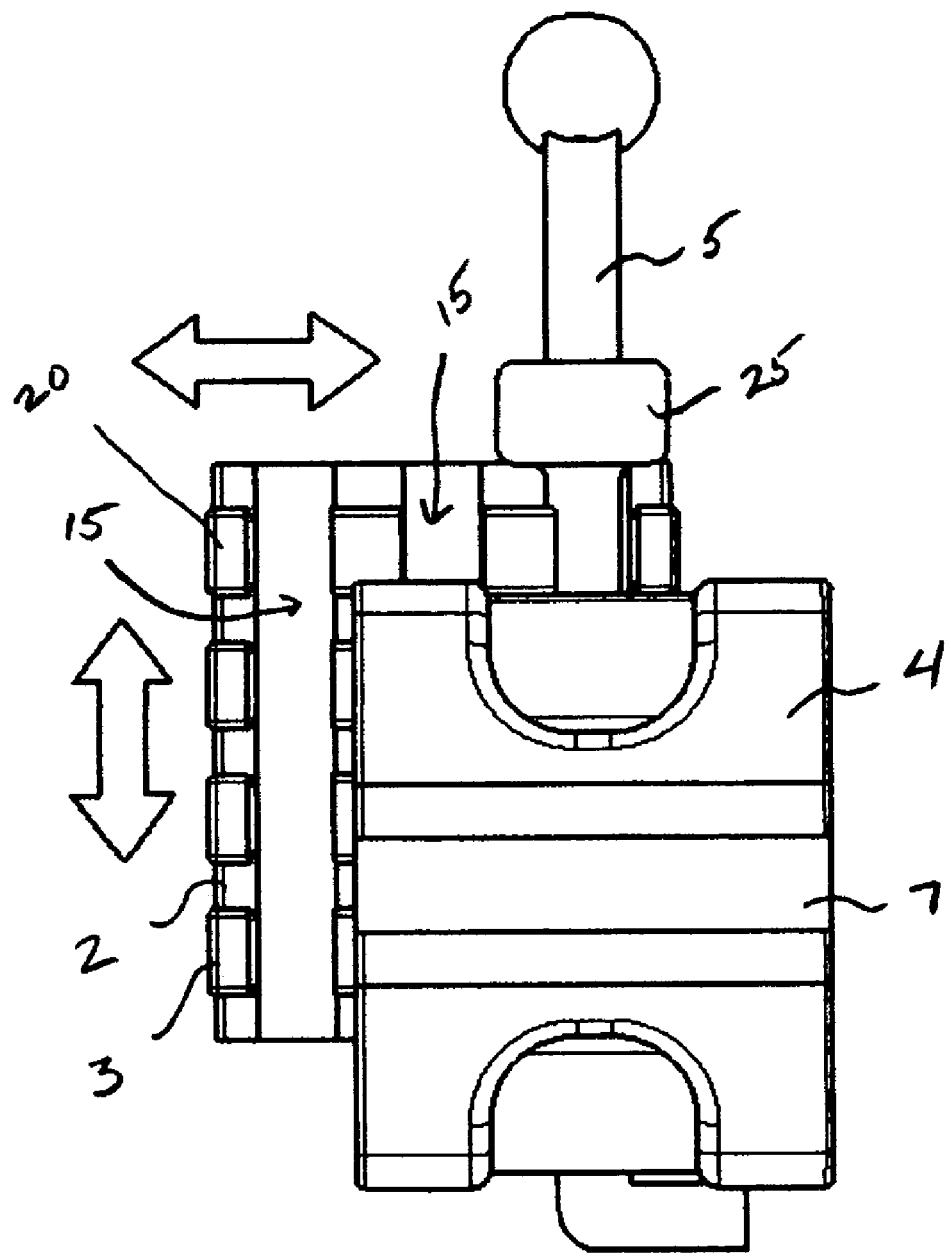
FIG. 8 is a frontal view of FIG. 7 showing the relationship and movement of the connecting plate relative to the base plate.

In another embodiment and as shown in FIGS. 7-8, the first device 3 of the second side 2b of the base plate 2 comprises a plurality of vertical and horizontal column of protrusions 20 and the second device 6 of the first side 4a of the connecting plate 4 comprises a plurality of vertical and horizontal column of protrusions 40, and the plurality of column of protrusions, 20 and 40 provides for a plurality of vertical and horizontal channels 15. The channels 15 provides the protrusion 20 and 40 to move during adjustment of the connecting plate 4 relative to the base plate 2 and the securing device 5 is situated with the channel 15 when the connecting plate 4 is locked into a certain position relative to the base plate 2. The protrusions 20 and 40 are designed to move vertically and horizontally within the channels 15 during the adjustment of the connecting plate 4 relative to the base plate 2. At least one of the protrusions 40 of the connecting plate 4 and at least one of the protrusions 20 of the base plate 2 engage one another when the securing device 5 locks the connecting plate 4 to the base plate 2.

The protrusions 20 and 40 of the base plate 2 and the connecting plate have geometric shapes, and at least one of the protrusions 20 of the base plate 2 has a geometric shape that creates a retentive undercut with the opposing geometric shape of at least one of the protrusions 40 of the connecting plate 4.

Figure 9:
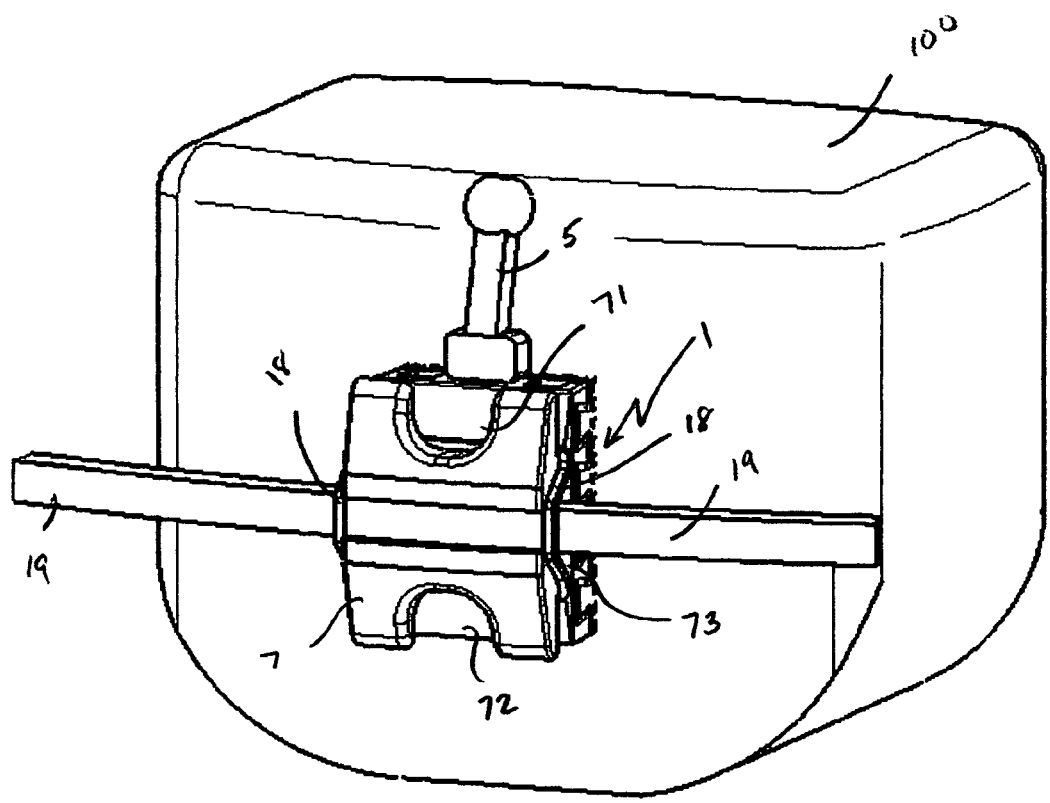
FIG. 9 is a perspective view of the orthodontic system of the present invention fully assembled on a patient's tooth.

FIG. 9 shows the orthodontic system 10 of the present invention assembled onto the tooth 100 of a patient. The tooth engaging side 2a of the base plate 2 is generally concave to conform with the curvature of a tooth 100. The orthodontic device 7 comprises at least two u-shaped protrusions, 71 and 72 respectively, on opposing ends 7a and 7b respectively; and a central cavity 73 for receiving a wire 19. At least one rubber band or steel ligature 18 is used to secure the wire 19 to the orthodontic device 7 within the cavity 73. The orthodontic device 7 is attached to the connecting plate 4 which is secured to the base plate 2 with the pin 5.

Figure 10:
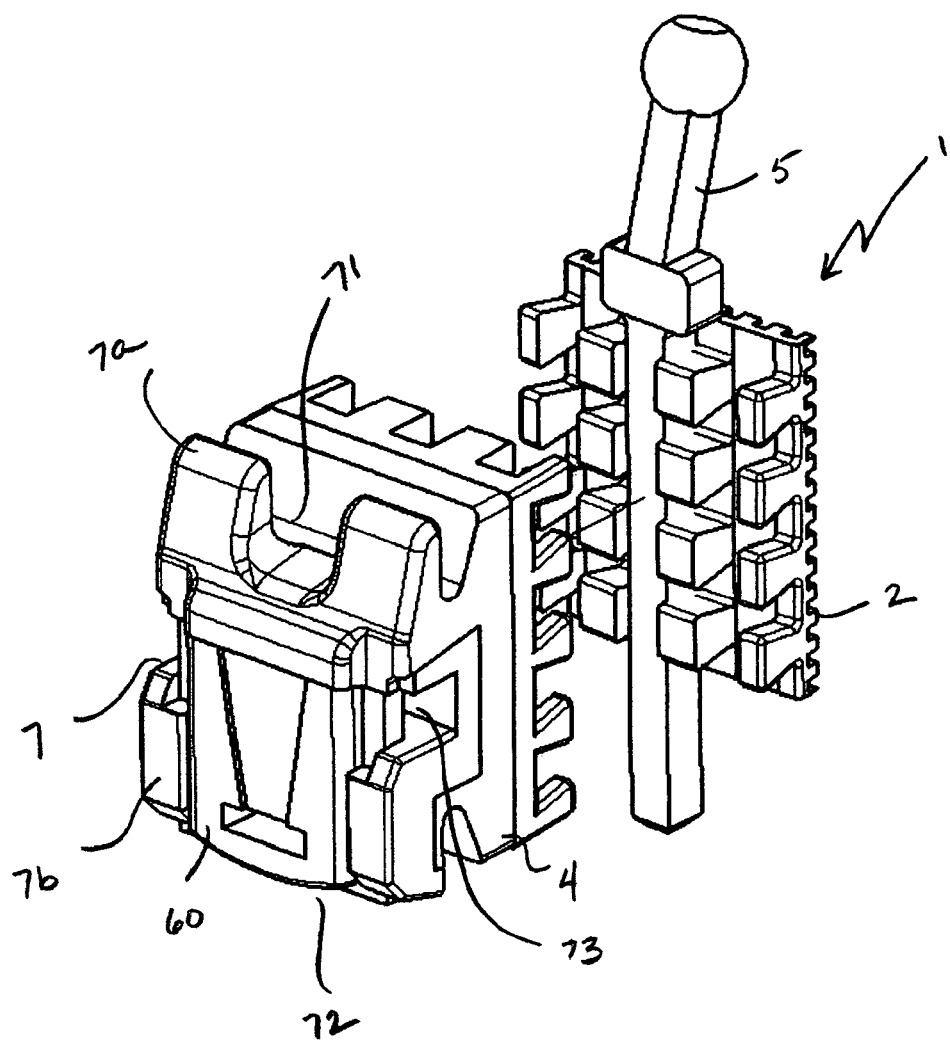
FIG. 10 depicts an exploded view of another embodiment of the orthodontic apparatus of the present invention with a connecting plate that has an opening and closing door.
Figure 11:
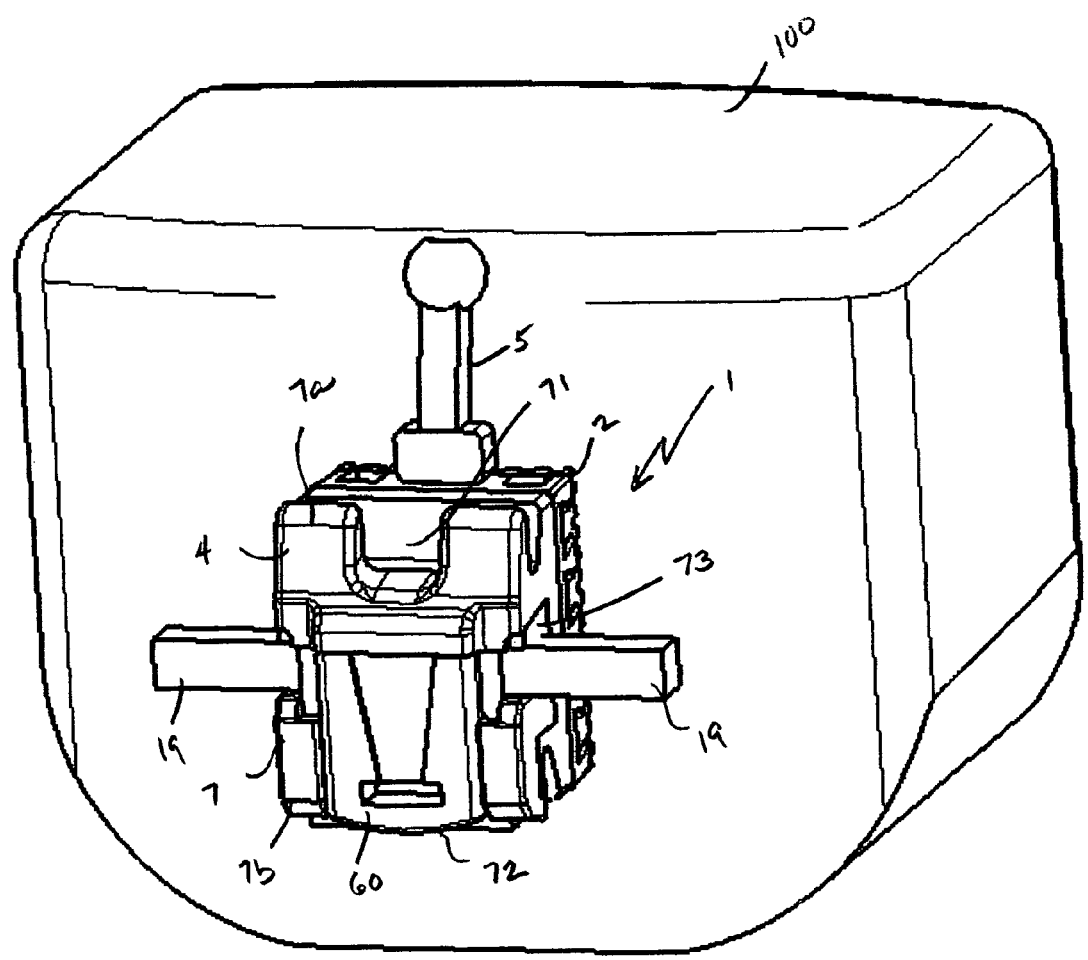
FIG. 11 is a perspective view of FIG. 9 fully assembled on a patient's tooth.
Figure 12:
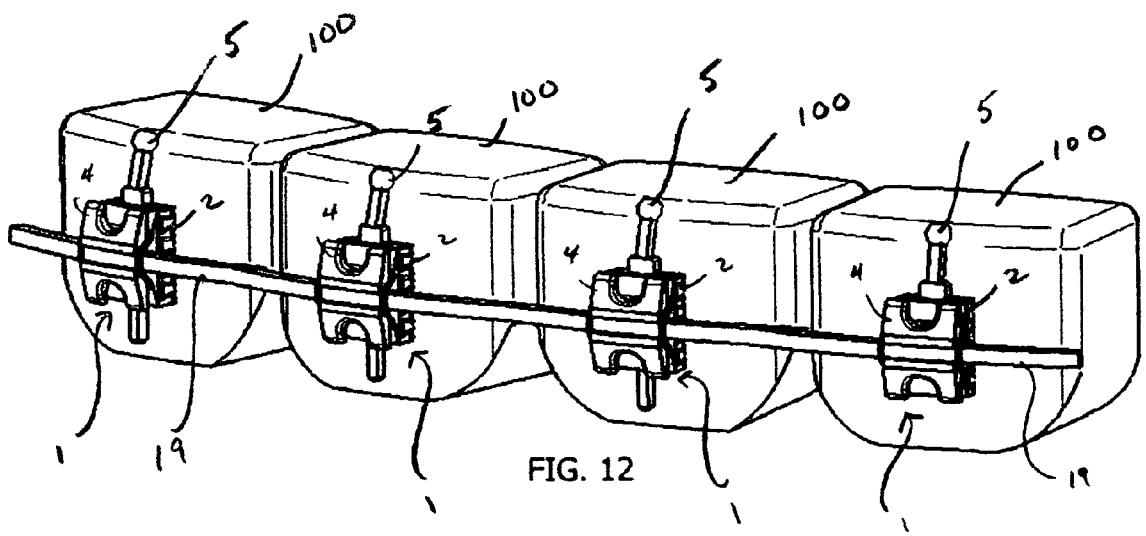
FIG. 12 is a perspective view of system of the present invention fully assembled on a patient's teeth.

FIGS. 10-12 depict another embodiment of the present invention wherein the orthodontic device 7 has a door 60 for enclosing the central cavity 73 to thereby lock the wire 19 into place. The orthodontic device 7 comprises at least two u-shaped protrusions, 71 and 72 respectively, on opposing ends 7a and 7b respectively; and a central cavity 73 for receiving a wire 19. The orthodontic device 7 is attached to the connecting plate 4 which is secured to the base plate 2 with the pin 5. FIGS. 11-12 shows the apparatus 1 assembled onto a patient's teeth 100.

Figure 13:
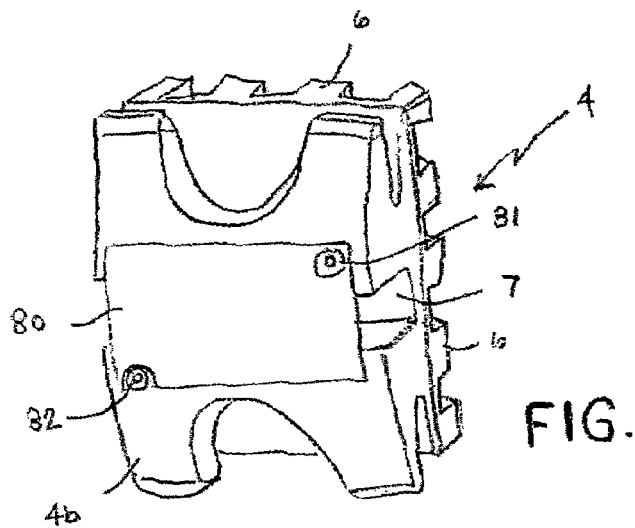
FIG. 13 is a perspective view of the self-ligating bracket of the present invention in a closed position.
Figure 14:
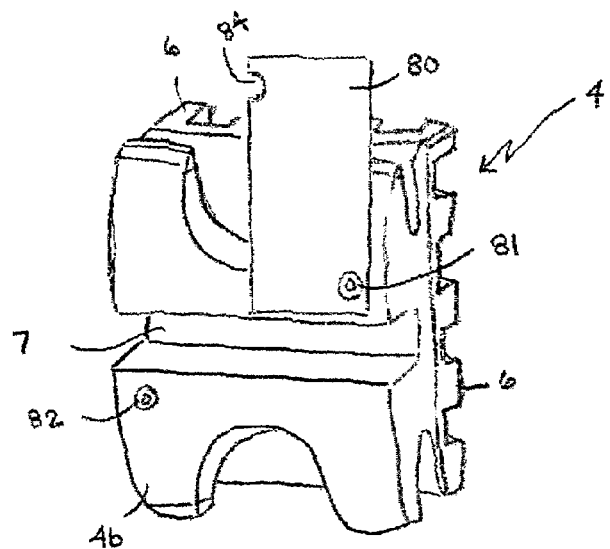
FIG. 14 is a perspective view of the self-ligating bracket of the present invention in an opened position.
Figure 15:
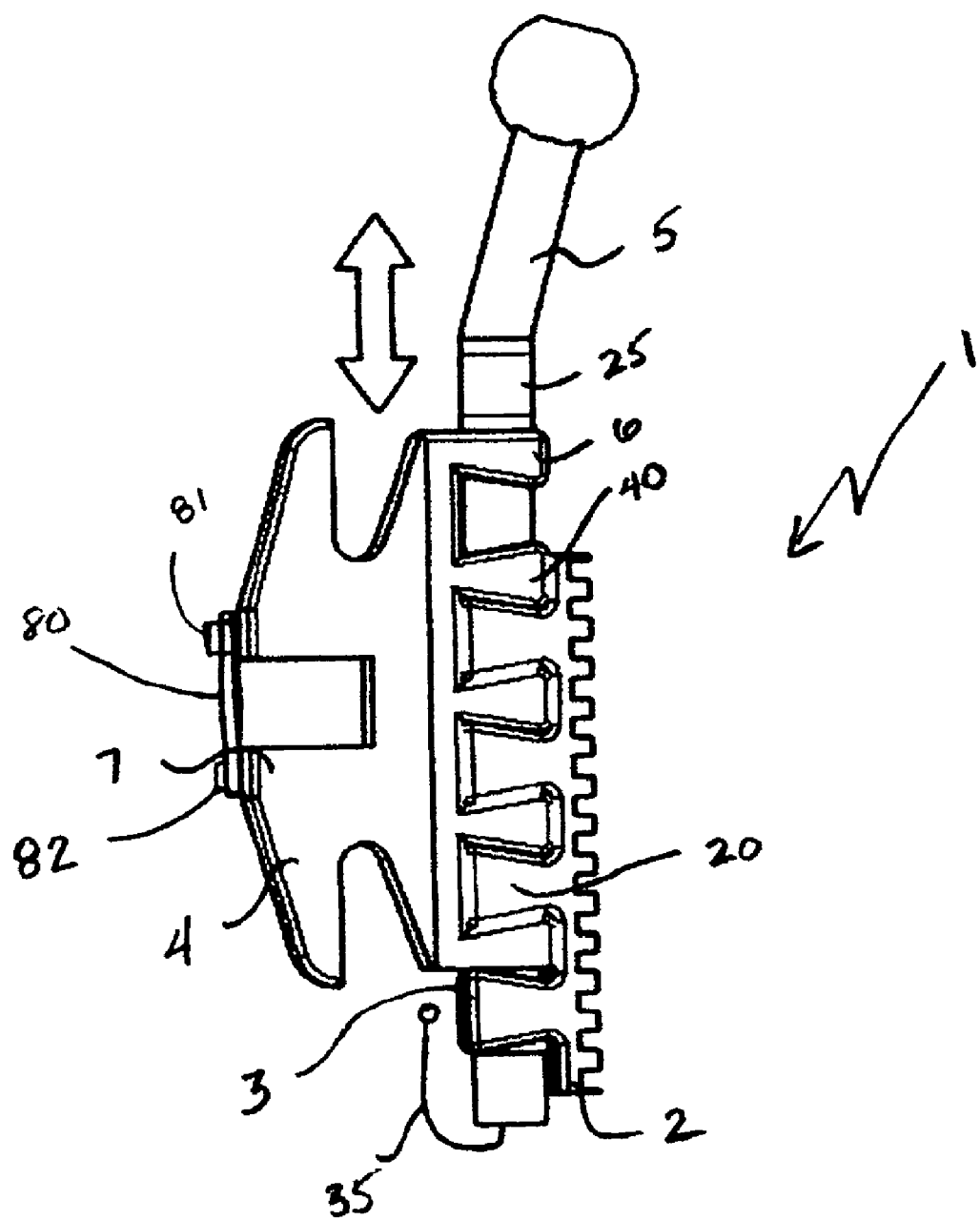
FIG. 15 is a side view of the self ligating bracket system of the present invention.
Figure 19:
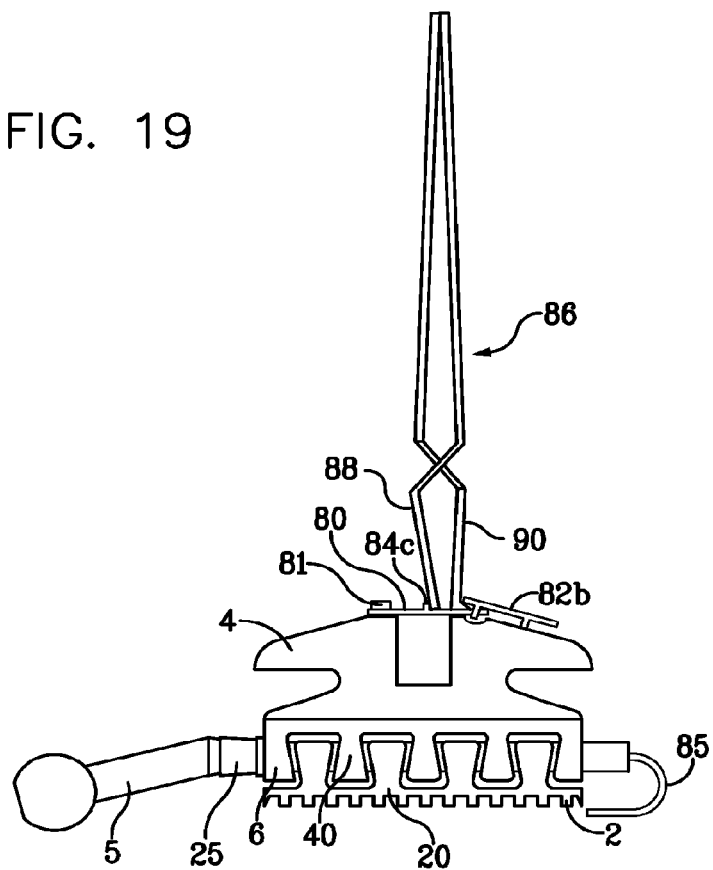
FIG. 19 is a side view of self ligating bracket with locking system showing a bracket opening instrument in use.

Referring now to FIGS. 13-15, the present invention provides for a bracket housing or connecting plate 4 comprising at least two opposing sides, a rear side being a tooth engaging side and a front side 4b having a cavity 7 for receiving a wire (not shown); and a cover plate 80 pivotally attached to the front side 4b of said bracket housing 4, the cover plate 80 is designed to be moveable from an open to a closed position to secure and hold the wire within the cavity 7 of said front side 4b of the bracket housing 4.

The front side 4b of the bracket housing 4 comprises a protrusion 82. The cover plate 80 comprises an indentation 84 for receiving the protrusion 82 during the closed position. The cover plate 80 is attached to a pivot point 81 attached to the front side 4b of the bracket housing 4.

The cover plate 80 is moved in a downward direction to the closed position when the bracket is placed on a lower tooth of patient's mouth and the cover plate 80 is moved in an upward direction to the closed position when the bracket is placed on an upper tooth of patient's mouth. In all other respects, the connecting plate is as described above.

FIGS. 16-19 depict another embodiment of a bracket housing or connecting plate 4 of the present invention showing a cover plate 80 pivotally attached to the front side 4b of a bracket in both the open and closed position. The cover plate 80 is designed to be movable from an open to a closed position to secure and hold the wire within the cavity 7 of said front side 4b of the bracket housing 4.

The front side 4b of the bracket housing 4 comprises a cover plate locking device first member, for example, spring clip 82b. The cover plate 80 comprises a cover plate locking device second member, for example, an opening 84b for receiving the spring clip 82b during the closed position. A ridge 84c is located just above the opening 84b and is used to engage an opening tool 86, for example, a bracket door opening instrument, for unlocking the cover plate 80 from the closed position. In a preferred embodiment, spring clip 82b comprises a first end 92 being attached to the bracket housing 4 and a second end 94 having a protrusion 82d for engaging the aperture 84b of the cover plate 80 during the locked position.

The cover plate 80 is moved in a downward direction to the closed position when the bracket is placed on a lower tooth of a patient's mouth and the cover plate 80 is moved in an upward direction to the closed position when the bracket is placed on an upper tooth of a patient's mouth.

As the cover plate 80 is moved into the closed position, spring clip 82b is displaced from bracket housing 4b as cover plate 80 slides under spring clip 82b. Upon cover plate 80 reaching it fully closed position, spring clip 82b engages opening 84b to lock cover plate 80 in its closed position. To open cover plate 80, opening instrument 86 is used to apply opening forces to ridge 84c, thereby causing spring clip 82b to disengage from opening 84b and allowing cover plate 80 to move to its open position.

Figure 20:
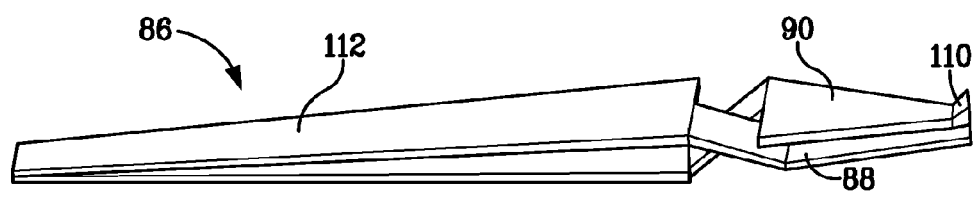
FIG. 20 is a perspective view of a bracket opening instrument in a passive state for disengaging a locking member.
Figure 21:
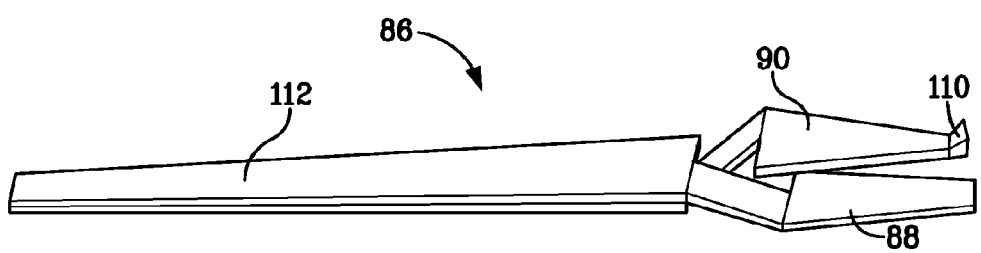
FIG. 21 is a perspective view of an instrument in an active state for disengaging a locking member.

As depicted in FIGS. 20 and 21, preferably, instrument 86 comprises a handle 112 and two legs 88, 90, for example, cross-over legs. The first leg 88 contacts ridge 84c and the second leg 90 disengages the spring clip 82b from the aperture 84b of the cover plate 80, for example, by sliding wedge 110 positioned at the end of second leg 90 under spring clip 82b.

FIG. 20 depicts instrument 86 in a passive, resting state and FIG. 21 depicts instrument 86 after it has been activated. Due to its cross-over design, once first leg 88 is positioned against ridge 84c, as the handle 112 is squeezed, instrument 86 is activated, thereby causing wedge 110 to slide under spring clip 82b.

As explained above, during a course of therapy, the bracket may need to be repositioned. The novel bracket holder 87 described below was developed to deal with the new challenges posed by the interlocking connector of my novel bracket system. Grasping the connector plate 4 (FIG. 1) without also inadvertently grasping the base plate 2 (FIG. 1) becomes very difficult, if not impossible using known bracket holders. If the base plate 2 is grasped, repositioning of the connector plate 4 is impossible because the base plate 2 is fixed to the tooth.

By using the bracket holder of the present invention, the clinician is able to easily grasp the connector plate 4 and move it up or down, right or left, without also grasping the base plate 2. Since the brackets themselves are very small, ease of manipulation is important to the success of my system.

Figure 22:
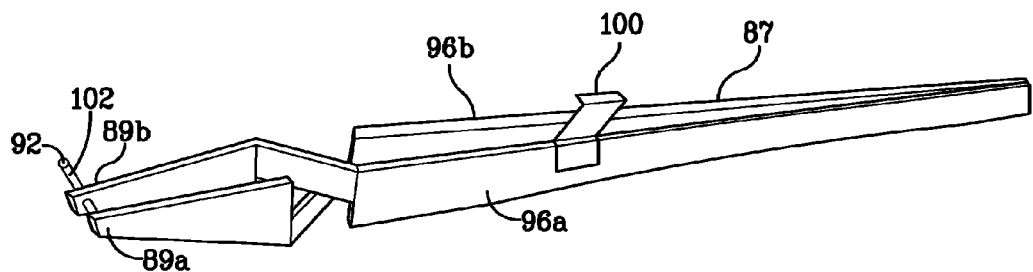
FIG. 22 is a perspective view of a bracket holder in a bracket engaging state.
Figure 23:
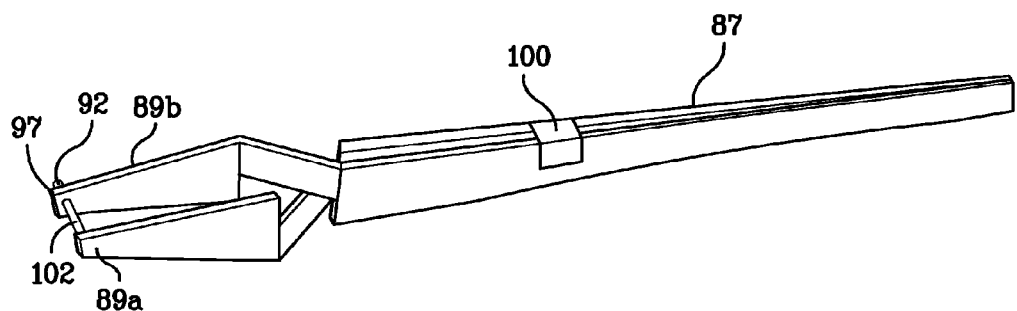
FIG. 23 is a perspective view of a bracket holder in a storage state.

FIGS. 22 and 23 depict a first embodiment of the bracket holder 87 of the present invention in both an open and closed position. Preferably, the bracket holder 87 comprises a handle comprising cross over legs, for example first leg 96a and second leg 96b. Optional, but preferred member, for example, hinge clip 100 mounted to handle first leg 96*a* allows the bracket holder beaks 89*a*, 89*b* to spring closed when hinge clip 100 is in an open position (FIG. 22). When the hinge clip 100 is in a closed position, for example, engaging handle second leg 96*b* (FIG. 23), the beaks 89*a*, 89*b* are sprung open allowing engagement of the connecting plate 4 (FIG. 1), described in detail below. At the same time, a depth limiter, for example, wire 102, is protected from being deformed during storage of the bracket holder 87. When the hinge clip 100 is closed (holding beaks 89*a*, 89*b* open), the wire 102 does not extend past a second beak 89*b*, thereby preventing the wire 102 from becoming bent while stored. In remaining open, the beaks 89*a*, 89*b* protect the integrity of the wire 102 during storage.

The wire 102, for example, an 0.018 stainless steel wire, is attached at a first end to a first beak 89*a*. A second end is slidably engaged through a hole 97 fabricated in second beak 89*b*. Wire 102 is positioned at a limiting depth from the end of the beaks 89*a*, 89*b*, preferably equal to the depth of the central cavity 73 (FIG. 10). The depth is preferably about 0.030", which is the depth of conventional and self-ligating bracket slots for 0.018×0.030 and 0.022×0.030 standard bracket prescriptions. The wire 102 has a stop 92, for example, a round ball, at its second end, used to limit the amount of opening between the two beaks 89*a*, 89*b*. In a preferred embodiment, the wire is normal to the contact surfaces, however any angle that allows for engagement with the central cavity is acceptable.

Figure 24:
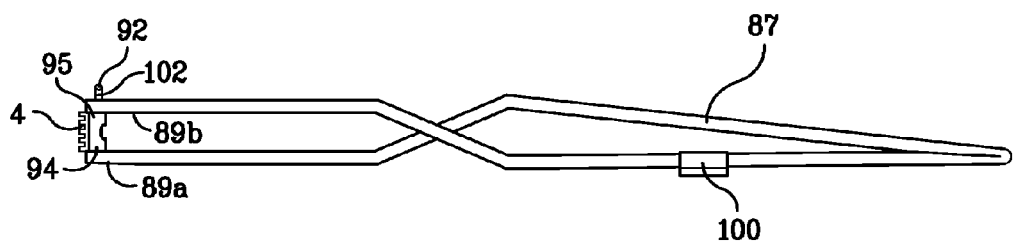
FIG. 24 is a side view of a bracket holder engaging a bracket connector plate.
Figure 25:
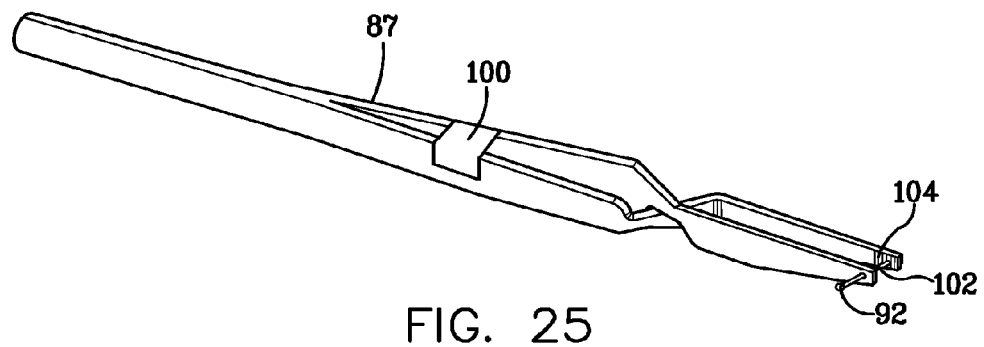
FIG. 25 is a perspective view of a bracket holder depicting the internal serrations.

FIG. 24 depicts a connector plate 4 engaged by the beaks 89*a*, 89*b* of the bracket holder 87. When depth limiting wire 102 is seated within central cavity 73 (FIG. 10), beaks 89*a*, 89*b* engage the connecting plate 4, for example, by squeezing bracket wings 94, 95 but are prevented from grasping base plate 2 (FIG. 1), thereby permitting connecting plate 4 to be repositioned as described above. Optionally, as depicted in FIG. 25, interior of beaks 89*a*, 89*b* may comprise serrations 104 to improve their grasping ability.

In this manner, the novel bracket holder of the present invention allows for easy and rapid grasping, moving and ultimately re-positioning of the connector plate 4.

In use, the hinge clip 100 is open allowing the clinician to spread the beaks 89*a*, 89*b* by squeezing the handles 96*a*, 96*b* together to position the beaks 89*a*, 89*b* over the connector plate 4. The engagement of the depth limiting wire 102 within the central cavity 73 prevents the beaks 89*a*, 89*b* from inadvertently grasping base plate 2. Upon release of the handles 96*a*, 96*b*, bracket holder 87 engages connector plate 4, thereby allowing the bracket to be positioned without disturbing the base plate 2 which is affixed to the tooth.

Figure 26:
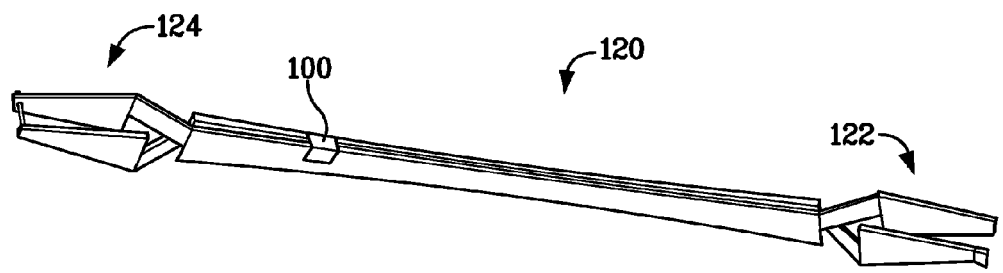
FIGS. 26 and 27 are perspective views of a double ended instrument.
Figure 27:
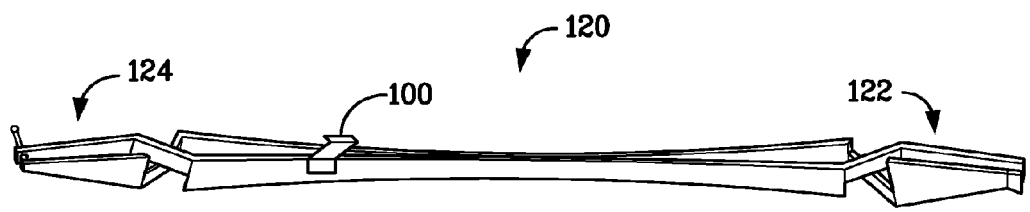

In another embodiment depicted in FIGS. 26 and 27, the operative features of the opening instrument 86 and the bracket holder 87 described above are combined into a single instrument 120. FIG. 26 depicts the opening instrument end 122 in an activated state and the bracket holder end 124 in a non-grasping, storage state with the hinge clip 100 closed. FIG. 27 depicts the opening instrument end 122 in a passive, resting state and the bracket holder end 124 in a grasping state with the hinge clip 100 open.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

What is claimed is:

1. An orthodontic system comprising a bracket and a bracket holder:
   the bracket comprising;
   a base plate comprising opposing sides, a first side being a tooth engaging side and a second side comprising at least two base plate protrusions positioned in a height wise base plate axis and at least two base plate protrusions positioned in a widthwise base plate axis, the base plate protrusions having a plurality of base plate spaces between them forming intersecting base plate channels;
   a connecting plate having opposing sides, a first side comprising at least two connecting plate protrusions positioned in a height wise connecting plate axis and at least two connecting plate protrusions positioned in a widthwise connecting plate axis, the connecting plate protrusions having a plurality of connecting plate spaces between them forming intersecting connecting plate channels; a second side comprising a central cavity; and
   a securing device for locking the connecting plate to a desired position onto the base plate,
   wherein the base plate protrusions mechanically engage and are freely movable within the connecting plate channels and the connecting plate protrusions mechanically engage and are freely movable within the base plate channels while the base plate and the connecting plate are engaged, such that separation of the base plate and connecting plate can occur during an adjustment phase;
   the securing device mechanically engages a channel formed by the engaging base plate and connecting plate to prevent further free movement and separation once the desired position is obtained; and
   at least one of the protrusions of the base plate has a geometric shape that creates a retentive undercut with an opposing geometric shape of at least one of the protrusions of the connecting plate to form the mechanical engagement; and
   the bracket holder comprising;
   a handle having a first and second end;
   a first and second leg extending from the handle second end, each leg having opposing distal ends;
   a single planar beak situated at each of the distal ends to engage the bracket; and
   a depth limiter affixed to one leg for limiting the amount of engagement of the bracket by the beak;
   wherein the depth limiter comprises a depth limiting stop attached to a beak for receiving by the central cavity of the bracket, such that when the depth limiting stop is fully seated within the central cavity, the beak does not extend beyond the bracket.

2. The system of claim 1 wherein the depth limiting stop comprises a wire having opposing ends, a first end of the wire being attached to a second beak and a second end of the wire designed to pass through an aperture on a first beak, the wire for receiving by the central cavity of the bracket, the wire first affixed to the second beak at a predetermined location such that when the wire is fully seated within the central cavity, the first and second beaks do not extend beyond a predetermined location of the bracket.

3. The system of claim 2 wherein the second end of the wire comprises a wire stop.

4. The system of claim 3 wherein the wire stop is designed to determine the maximum distance between the first and second beak.

5. The system of claim 3 wherein the wire stop is a round ball and is designed to determine the maximum achievable separation of the-first and second beak in an open position.

6. The system of claim 2 wherein the legs are designed to be squeezed together to allow the first and second beak to move away from one another and to allow a greater portion of the second end of the wire to pass through the aperture.

7. The system of claim 1 wherein the handle is squeezed to allow a first and second beak to open in a squeezed position and the handle is released to allow the first and second beaks to close in a released position.

8. The system of claim 1 wherein at least a portion of each of the legs adjacent to the distal ends cross over to create the handle.

9. The system of claim 1 further comprising a member affixed to a first movable portion of the bracket holder which when engaged with a second movable portion of the bracket holder holds the beaks apart.

10. An orthodontic system comprising a bracket and a bracket holder:
the bracket comprising,
a base plate comprising opposing sides, a first side being a tooth engaging side and a second side comprising a plurality of base plate protrusions positioned in a height wise base plate axis and a plurality of base plate protrusions positioned in a widthwise base plate axis, the base plate protrusions having a plurality of base plate spaces between them forming intersecting base plate channels;
a connecting plate having opposing sides, a first side comprising a plurality of connecting plate protrusions positioned in a height wise connecting plate axis and a plurality of connecting plate protrusions positioned in a widthwise connecting plate axis, the connecting plate protrusions having a plurality of connecting plate spaces between them forming intersecting connecting plate channels; and
a securing device for locking the connecting plate to a desired position onto the base plate,
wherein the base plate protrusions mechanically engage and are freely movable within the connecting plate channels and the connecting plate protrusions mechanically engage and are freely movable within the base plate channels while the base plate and the connecting plate are engaged, such that separation of the base plate and connecting plate can occur during an adjustment phase;
the securing device mechanically engages a channel formed by the engaging base plate and connecting plate to prevent further free movement and separation once the desired position is obtained; and
at least one of the protrusions of the base plate has a geometric shape that creates a retentive undercut with an opposing geometric shape of at least one of the protrusions of the connecting plate to form the mechanical engagement; and
the bracket holder comprising;
two legs having opposing ends, the legs being attached to one another, each of the legs comprising at least one beak situated at a first end of each of the legs, a first beak having at least one aperture, a second beak comprising at least one wire having opposing ends, the one end of the wire being attached to the second beak and the second end of the wire designed to pass through the aperture on the first beak, the wire designed to support the bracket during installment and adjustment of the bracket such that the legs do not extend beyond the bracket, a second end of each of the legs together forming a handle.

11. The system of claim 10 wherein the wire is generally normal to the second beak.

12. The system of claim 10 wherein the second end of the wire comprises a stop.

13. The system of claim 12 wherein the stop determines the maximum achievable distance between the first and second beaks.

14. The system of claim 10 wherein the legs of the handle are designed to be squeezed together to allow the first and second beaks to move towards one another and to allow a greater portion of the second end of the wire to pass through the aperture of on the second beak.

15. An orthodontic system comprising:
an instrument for disengaging a self-ligating bracket cover plate comprising;
a handle having a first and second end;
a first and second leg extending from the handle second end, each leg having opposing distal ends;
the first leg distal end designed to engage the cover plate and the second leg distal end designed to engage a cover plate locking device affixed to the bracket, such that the cover plate is disengaged from the locking device as the distal ends move away from one another; and
a bracket comprising
a base plate comprising opposing sides, a first side being a tooth engaging side and a second side comprising at least two base plate protrusions positioned in a height wise base plate axis and at least two base plate protrusions positioned in a widthwise base plate axis, the base plate protrusions having a plurality of base plate spaces between them forming intersecting base plate channels;
a connecting plate having opposing sides, a first side comprising at least two connecting plate protrusions positioned in a height wise connecting plate axis and at least two connecting plate protrusions positioned in a widthwise connecting plate axis, the connecting plate protrusions having a plurality of connecting plate spaces between them forming intersecting connecting plate channels; a second side comprising the cover plate and locking device; and
a securing device for locking the connecting plate to a desired position onto the base plate,
wherein the base plate protrusions mechanically engage and are freely movable within the connecting plate channels and the connecting plate protrusions mechanically engage and are freely movable within the base plate channels while the base plate and the connecting plate are engaged, such that separation of the base plate and connecting plate can occur during an adjustment phase;
the securing device mechanically engages a channel formed by the engaging base plate and connecting plate to prevent further free movement and separation once the desired position is obtained; and
at least one of the protrusions of the base plate has a geometric shape that creates a retentive undercut with an opposing geometric shape of at least one of the protrusions of the connecting plate to form the mechanical engagement.

16. The system of claim 15 wherein the legs are designed to be squeezed together to move the distal ends away from one another.

17. The system of claim 16 wherein the second leg distal end further comprises a wedge and the locking device comprises a spring clip, the wedge designed to slide under and disengage the spring clip as the distal ends move away from one another.

18. The system of claim 15 wherein at least a portion of each of the legs adjacent to the distal ends cross over to create the handle.

19. An orthodontic system comprising an instrument and a bracket:

the instrument comprising;
a handle having a first and second end;
a first and second leg extending from the handle first end, each leg having opposing distal ends;
a single planar beak for engaging the bracket situated at each of the distal ends; and
a depth limiter affixed to at least one leg for limiting the amount of engagement of the bracket by the beak; and
a first and second leg extending from the handle second end, each leg having opposing distal ends;
the first leg opposing distal end designed to engage a self-ligating bracket cover plate and the second leg opposing distal end designed to engage a cover plate locking device affixed to the bracket, such that the cover plate is disengaged from the locking device as the opposing distal ends move away from one another
wherein the depth limiter comprises a depth limiting stop attached to a beak for receiving by a central cavity of the bracket, such that when the depth limiting stop is fully seated within the central cavity, the beak does not extend beyond the bracket; and
a bracket comprising
a base plate comprising opposing sides, a first side being a tooth engaging side and a second side comprising at least two base plate protrusions positioned in a height wise base plate axis and at least two base plate protrusions positioned in a widthwise base plate axis, the base plate protrusions having a plurality of base plate spaces between them forming intersecting base plate channels;
a connecting plate having opposing sides, a first side comprising at least two connecting plate protrusions positioned in a height wise connecting plate axis and at least two connecting plate protrusions positioned in a widthwise connecting plate axis, the connecting plate protrusions having a plurality of connecting plate spaces between them forming intersecting connecting plate channels: a second side comprising the central cavity, the cover plate, and the locking device; and
a securing device for locking the connecting plate to a desired position onto the base plate,
wherein the base plate protrusions mechanically engage and are freely movable within the connecting plate channels and the connecting plate protrusions mechanically engage and are freely movable within the base plate channels while the base plate and the connecting plate are engaged, such that separation of the base plate and connecting plate can occur during an adjustment phase;
the securing device mechanically engages a channel formed by the engaging base plate and connecting plate to prevent further free movement and separation once the desired position is obtained; and
at least one of the protrusions of the base plate has a geometric shape that creates a retentive undercut with an opposing geometric shape of at least one of the protrusions of the connecting plate to form the mechanical engagement.

20. The system of claim 19 wherein
the depth limiter comprises a wire having opposing ends, a first end of the wire being attached to a second beak and a second end of the wire designed to pass through an aperture on a first beak, the wire being received by a central cavity of the bracket, the wire first end affixed to the second beak at a predetermined location such that when the wire is fully seated within the central cavity, the first and second beaks do not extend beyond a predetermined location of the bracket;
the second end of the wire has a stop on the end;
the handle first end legs are designed to be squeezed together to allow the first and second beaks to move away from one another and to allow a greater portion of the second end of the wire to pass through the aperture;
the handle first and second end legs are each designed to be squeezed together to move the distal ends away from one another.

21. The system of claim 20 wherein at least a portion of each of the legs adjacent to the opposing distal ends cross over to create the handle, the handle first end further comprises a member affixed to a first movable portion which when engaged with a second movable portion holds a first and second beak apart; the second leg distal end further comprises a wedge and the locking device comprises a spring clip, the wedge designed to slide under and disengage the spring clip as the opposing distal ends move away from one another; and at least a portion of the first handle legs cross over each other and a portion of the second handle legs cross over each other to create the handle.

* * * * *